United States Patent [19]

Rhodes

[11] Patent Number: 5,662,924
[45] Date of Patent: Sep. 2, 1997

[54] WOUND DRESSING

[75] Inventor: Tanya Rhodes, Harbour Bluffs, Fla.

[73] Assignee: Smith & Nephew plc, United Kingdom

[21] Appl. No.: 479,558

[22] Filed: Jun. 7, 1995

Related U.S. Application Data

[63] Continuation of Ser. No. 119,054, filed as PCT/GB92/00519, Mar. 20, 1992, published as WO92/16245, Oct. 1, 1992, abandoned.

[30] Foreign Application Priority Data

Mar. 21, 1991 [GB] United Kingdom ............... 9105995

[51] Int. Cl.$^6$ ...................................................... A61L 15/00
[52] U.S. Cl. .......................... 424/445; 424/449; 514/781; 514/944
[58] Field of Search ......................... 424/445, 449; 514/781, 944

[56] References Cited

U.S. PATENT DOCUMENTS

| 4,618,491 | 10/1986 | Kanematu | 424/81 |
| 5,082,663 | 1/1992 | Konishi | 424/445 |

FOREIGN PATENT DOCUMENTS

| 0206692 | 12/1986 | European Pat. Off. |
| 0272149 | 3/1992 | European Pat. Off. |
| 8400111 | 1/1984 | WIPO |

*Primary Examiner*—D. Gabrielle Phelan
*Attorney, Agent, or Firm*—Graham & James LLP

[57] ABSTRACT

A wound dressing containing a water-insoluble, water swellable cross-linked cellulose derivative, water and a polyol component wherein the dressing comprises a gel and the cellulose derivative comprises less than 10% by weight of the gel. The dressing is easy to apply and is believed to enhance moisture penetration of necrotic tissue and thus speed up debriding action in facilitating wound healing.

18 Claims, No Drawings

WOUND DRESSING

This application is a continuation of U.S. Ser. No. 08/119,054, filed as PCT/GB92/00519 Mar. 20, 1992 and published as WO92/16245, Oct. 1, 1992, now abandoned.

The present invention relates to wound dressings

Secreting skin wounds such as decubitus ulcers venous stasis ulcers, pressure sores, open surgical wounds and burns require a special combination of therapy and dressing since the physiological functions of the skin are absent or materially impaired. Various proposals have been made for the treatment of such wounds. In addition to the conventional textile dressings used in wound management, non-woven fabrics and a variety of other synthetic products have been used.

Necrotic tissue may only be left on a wound when it forms an inert protective layer beneath which, an excess of fluid does not collect. In all other cases, the necrotic tissue must be removed, since healing requires a bed of granulation tissue and this is never compatible with slough or dead tissue. The removal of necrotic tissue or slough may be achieved by surgical excision or by the use of topical debriding agents. Surgical excision requires general anaesthetic since local anaesthetic injections may carry infection deeper into the wound. Topical debriding agents include enzymatic preparations and chemical agents. Enzymatic preparations break down the tissue allowing it to be washed out of the wound, however, usually healthy tissue must be protected. Enzymatic preparations may be inactivated unless operated within a narrow pH range. Chemical debriding agents such as alkaline hypochlorite solutions when used on gauze, dry out and as the dressing is changed it pulls off a layer of eschar. However, wet-to-dry dressing changes are potentially very painful. Also it is a non-selective form of debridement removing both nonviable and healing epithelial tissue. Chemical cream debriding agents break down the necrotic tissue, but are also active against healthy skin. When using such creams the healthy skin normally has to be protected with a barrier cream.

Thus these known means or techniques for debridement all suffer from a number of disadvantages. A dressing which can obviate or mitigate the known disadvantages would be highly desirable. Thus a need exists for a dressing which can combine the actions of debridement and cleansing regardless of the extent of necrosis. The dressing would be able to break down necrotic tissue and to retain the resultant debris. Slough which is typically composed of dead leucocytes trapped in wound exudate and increases the risk of infection must also be removed. The dressing would aid the removal of any slough present and be able to hold large quantities of blood, serum and purulent matter and separate these secretions from subcutaneous tissue. It would provide at least a partial barrier to loss of body fluids and electrolytes, provide some release from pain and prevent drying of denuded subcutaneous tissue.

U.S. Pat. No. 4,226,232 discloses a gel wound dressing comprising a water absorbent hydrolysed starch-polyacrylonitrile graft copolymer and water for treating secreting skin wounds. The dressing is stated to significantly improve wound cleanliness and reduce accumulations of necrotic, dried secretions, in the depths of wounds and skin ulcers. It is not however a substitute for surgical debridement. If necrotic tissue is already present and eschar formation has already occurred, debridement with a scalpel or scissors is necessary for the full potential of the dressing to be realised.

United Kingdom Patent No. 2124487 discloses a composition for the treatment of wounds. The composition comprises a hydrolysed starch—polyacrylonitrile graft copolymer, of which in the range of from 5 to 90% of the carboxy groups have been neutralised with aluminium, containing within its matrix, an aqueous solution including from 2 to 50% by weight of a di- or poly-hydroxyalkane. The compositions are distinguished by an extraordinary imbibing or wicking action encouraging rapid healing of wounds as a result of the removal of water. However it has now been found that the shelf life of the product gel is not as long as is desirable.

These prior art dressings suffer from the disadvantage that in cases where necrotic tissue is already present and eschar formation has already occurred, they have no debriding activity.

The present invention therefore seeks to provide a dressing that will promote debridement where necrotic tissue is already present and eschar formation has already occurred. Such dressings are based upon cross-linked cellulose derivatives.

The use of dressings containing large amounts of cross-linked carbohydrates has been proposed for the absorption of exudate from highly exuding wounds such as venous ulcers and burns.

In EP-A-0207022 there is disclosed a method of stabilising aqueous dispersions of water-absorbent particles and a matrix-forming hydrophilic thickening agent wherein inter alia the dispersion comprises 30 to 70% by weight of alia particles or beads of a material such as a cross-linked carbohydrate wherein the particles retain substantially intact the water absorbency properties of the material when in the form of dry beads. Such preparations have use for the treatment of highly exuding wounds such as burns or ulcers where a high degree of absorbency is required. Such dressings would be totally unsuitable for use as a debriding dressing on necrotic wounds since the drying action, particularly where it is a rapid drying could result in trauma and stress to the patient. In complete contrast we have found that for effective debriding to take place little or no dehydration or, preferably some re-hydration of the wound is required.

Accordingly the present invention provides a wound dressing containing a water-insoluble, water-swellable cross-linked cellulose derivative, water and a polyol component wherein the dressing comprises a gel and the cellulose derivative comprises less than 10% by weight of the gel.

By gel is meant a three-dimensional network of a super absorbent polymer which interacts with aqueous solutions by swelling and retains a significant proportion of water within its structure. Preferably the polymer will be ready saturated with water.

For the purposes of this invention a super absorbent polymer is understood to mean a polymer absorbing at least ten times its own weight of water.

Suitable cross-linked cellulose derivatives include those of the hydroxy lower alkyl celluloses wherein the alkyl group aptly contains for 1 to 6 carbon atoms eg. hydroxyethylcellulose, hydroxypropylcellulose; and the carboxy-celluloses eg. carboxymethylhydroxyethylcellulose and carboxymethylcellulose.

Ionic cellulose derivatives such as the carboxy celluloses are suitable. Carboxymethylcellulose in the form of its sodium salt is a preferred cellulose derivative. It is readily available and is cheapest form of carboxymethylcellulose. However, other salt forms may also be used eg. lithium and potassium.

Carboxymethylcellulose may be prepared according to conventional methods. Thus it may be prepared by the reaction of cellulose with the sodium salt of chloroacetic acid in aqueous alkaline organic slurries. Thus cellulose is steeped in sodium hydroxide solution and the alkali cellulose is treated under controlled conditions with sodium monochloroacetate to form the sodium salt of carboxymethylcellulose and sodium chloride.

The carboxymethylcellulose may be cross-linked by forming chemical eg. ester or ether cross-linkages or thermal cross-linkages, depending on the mode of manufacture.

A carboxymethylcellulose which has been found to be particularly suitable for purposes of the present invention is the finely divided substantially water insoluble sodium carboxymethylcellulose Akucell SW3009-X181 available from Akzo Salt and Basic Chemicals.

Akucell SW 3009-X181 is substantially insoluble in water, but is able to absorb many times its own weight of water and other fluids. It can absorb up to 86 g water/g polymer. It has a bulk density of 0.4 to 0.7 g cm$^{-3}$. It has a particle size of less than 1000 micron. Preferably the particle size is less than 250 micron.

Polyols for use in the present invention are aptly water miscible and, more aptly are liquid at room temperature.

Polyols suitable for use in the present invention include dihydroxyalkanes such as glycols which have from 2 to 6 carbon atoms, for example, 1,2-dihydroxypropane, 2,3-dihydroxybutane and 3,4-dihydroxyhexane, 2,5-dihydroxyalkane, the diethylene and triethylene glycols. 1,2-dihydroxypropane (propylene glycol) is the preferred dihydroxyalkane for use in the dressings of the present invention.

Polyhydroxyalkanes of the general formula

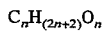

$$C_nH_{(2n+2)}O_n$$

in which n is a number from 3 to 6, are suitable for the preparation of a dressing of the invention and are, for example, glycerin, sorbitol, mannitol, adonite, ribite, dulcitol, erythritol and xylite.

A polyethylene glycol suitable as a polyol for the preparation of a dressing of the invention is a water-soluble one having a molecular weight in the range of from 200 to 600. A polypropylene glycol that may be used is water-soluble and preferably has a molecular weight of in the range of 200 to 450.

The dilution of the polyol is preferably effected by means of demineralised water. It is also possible to use a mixture of polyols.

The polyols act as humectants. They have the effect of reducing the partial vapour pressure of water so that the dressings do not dry out. As a result, adhesion to the wounds or edges of the wounds is avoided, so that the dressing may be removed without difficulty. Furthermore, they aid in the dispersion of the cellulose derivative in water during processing. They also render to the dressing physical properties which makes it more easy to apply. It is also believed that they enhance the moisture penetration of necrotic tissue and thus speed up the debriding action. In addition, it is believed that they may act as biostatic agents, stopping the growth of micro-organisms.

The polyol component may comprise up to 50% by weight of the gel. Suitably the polyol(s) is/are present in the range of from 10% to 30% by weight of the gel. Preferably the polyol(s) is/are present as about 20% by weight of the gel.

Suitably the cellulose derivative comprises at least 0.1% by weight of the gel. Generally the cellulose derivative is present in an amount of at least 2%. Aptly the gel will contain less than 6%, more aptly in the range of 2 to 4% of the cellulose derivative. Preferably the cellulose derivative comprises 3% by weight of the gel.

The dressings of the present invention may in addition, contain any additive and auxiliary substance (for example perfumes) customary for such compositions, as well as, in therapeutically active amounts, active substances(s) customarily used as wound treatment agents. Such active substances are, for example, antibacterial agents, antimycotics and local anaesthetics. Suitable antibacterial agents are sulphonamides, for example, suldacine and sulphatolamide, or antibiotics, for example penicillin and metronidazole. Suitable antimycotics are salicylic acid and derivatives thereof, for example salicylhydroxamic acid, salicylamide, miconacol and isoconacol. Suitable local anaesthetics are alkaloids, for example morphine, and esters of p-aminobenzoic acid, for example the methyl ester and the ethyl ester.

The dressing may also contain additional debriding agents eg. enzymatic debriding agents and/or growth factors.

The pH of the gel should lie in a therapeutically desirable range. Preferably the pH should not be lower than pH 6. Suitably the pH on the alkaline side should not have a value greater than pH 8.5. Aptly the pH value is within the range of pH 6 to pH 8.5, more aptly in the range of pH 6.5 to pH 7.5. The pH may be adjusted if necessary in the customary manner, for example, by adding a measured amount of acid or alkali.

Where the wound dressing of the present invention contains a gel, the elasticity of the gel is such that the gel may be readily applied to the wound and yet not flow out. Thus the physical properties of the gel are such that it easily reaches into wound cavities and crevices and thus comes into intimate contact with the area to be treated. This feature not only ensures that all areas to be treated come into contact with the gel but it also reduces or in some cases eliminates the pain experienced by the patient during application and removal of the gel from the wound as compared to prior art gel dressings.

In those embodiments of the invention where the gel is the sole component of the dressing, the gel should suitably have an elasticity greater than 300 Newtons/M$^2$. Suitably the elasticity of the gel is less than 3500 Newtons/M$^2$. Aptly the elasticity of the gel is in the range of from 500 to 3000 Newtons/M$^2$. More aptly the elasticity should be in the range of from 1000 to 2500 Newtons/M$^2$. Preferably the elasticity of the gel is in the range of from 1500 to 2500 Newtons/M$^2$.

In those embodiments of the invention where the dressing comprises additional components to the gel, eg. a backing material as hereinafter described, the gel may have an elasticity greater than 300 Newtons/M$^2$. Suitably the elasticity of the gel may be less than 13,000 Newtons/M$^2$.

The elasticity of the dressing may be measured by a rheometer. A suitable rheometer is eg. the Carri-Med 100 CLF rheometer. Suitable test parameters for use of this equipment to measure the elasticity of gels is as follows:

Temperature—25.0° C.

Plates—4.0 cm stainless steel parallel

Mode—Oscillation. Reading @ 5 Hz

The materials comprising the gel of the present invention are primarily debriding agents.

Thus the materials, in combination break down necrotic tissue and eschar. The debridement exhibited by the dressing of the present invention is believed to be due to the ability of the gel to release water to a wound to be treated. Thus water moves in the direction from the gel to the dressing.

The movement of the water from the dressing to the wound is believed to be as a consequence of the fact that the cross-linked cellulose derivative almost completely saturated. However, it is not completely saturated this being evidenced by the fact that the gel is capable of absorbing some water under certain conditions. Thus the gel of the present invention may act as an absorbent where the wound is exuding. Generally highly necrotic wounds will not be highly exuding and therefore the gel will not tend act in its absorptive capacity to any great extent. However, wounds comprising slough and/or some necrotic tissue will tend to be more highly exuding and in these cases the gel will tend to combine its absorptive and debriding actions.

Thus the gels of the present invention exhibit a bi-directional movement of water ie. the first direction being the conventional direction associated with absorbent wound dressings ie. from the wound towards the dressing and the second direction being in the opposite direction ie. away from the dressing and towards the wound.

The movement of water from the gel to the wound as described above is thought to be responsible for the debriding and/or rehydrating effect of the gel of the present invention.

In use the gel of the present invention is almost completely swollen, thus when it comes into contact with a necrotic wound where there is little exudate, the tendency is for the gel to act as a rehydrating agent. The gel does not tend to act as an absorbing agent.

The rehydrating action of the dressing of the present invention is believed to be intimately associated with the physical structure of the gel. Thus the gel comprises a homogeneous mixture of a cross-linked cellulose derivative wherein the cellulose derivative particles are almost completely swollen.

According to another aspect of the invention, there is provided a process for making the gel dressing of the invention which comprises mixing a water-insoluble, water-swellable cross-linked cellulose derivative, water and polyol component.

The gel components may be mixed by adding all of the components to a mixer eg. a Ystral mixer and mixing continuously until a homogeneous mixture is formed. Alternatively the cross-linked cellulose derivative may be pre-blended with some or all of the polyol component. The pre-blend may then be added to the remainder of the component of the gel and mixed until homogeneity is attained.

In cases where a homogeneous mixture is not obtained as a result of mixing the components of the dressing, it may be necessary to submit the mixture to a mechanical means of achieving homogeneity eg. a milling step. A milling step may be carried out using a colloid mill eg. a Probst and Class colloid mill.

The gel is generally sterilised prior to use. The gel may be sterilised before being packaged and subsequently may be packaged aseptically. Preferably the gel may be sterilised after it has been packaged. Sterilisation may be affected by any of the known sterilising methods. However, the preferred means of the sterilisation is steam sterilisation.

In use the dressing of the invention may be employed to treat a wound, particularly a wound containing necrotic tissue, by a method comprising applying the dressing directly to a wound or area of the body to be treated. The wound may be prepared by irrigating with normal saline. Conveniently the gel component is supplied in sachet form eg. 25 g sachets. The sachet tear area may be swabbed with a suitable antiseptic prior to opening. The contents of the sachet are gently squeezed out of the sachet into or onto the wound. Due to the consistency of the dressing, application is very simple. If required, a sterile spatula or similar instrument may be used to smooth the gel into crevices and openings in the wound. Once enough gel has been applied (a minimum depth of 5mm should be ensured) the gel may optionally be covered with an additional absorbent material.

The gel may be used in conjunction with many absorbent materials. The condition of the wound determines the choice of absorbent material and the frequency of change.

In a further embodiment of the invention, an occlusive film such as a polyurethane film may be suitably employed as an secondary dressing. The occlusive film significantly increases moisture penetration of the necrotic tissue thus aiding the action of the gel. The film may be placed over the gel after the gel has been applied to the wound.

Additional absorption may be provided by using an absorbent pad, preferably of a non-adherent nature. The absorbent material may be placed over the gel after application of the gel to the wound.

According to a further embodiment of the invention the dressing comprises a gel wherein the gel comprises a water insoluble water swellable cross-linked cellulose derivative, water and a polyol component wherein the cellulose derivative comprises less than 10% by weight of the gel wherein the gel is a layer upon a backing layer. Suitable backing layers include an occlusive film such as polyurethane or an absorbent material eg. a polyurethane foam material.

To remove the dressing, the optional absorbent material if present, is first removed and the gel dressing of the invention is then easily removed by irrigating with normal saline.

The invention further provides a dressing in which the gel dressing hereinbefore described, may be combined with an absorbent material eg. any of the above mentioned absorbent materials to give a combined integral dressing combining the properties of the gel dressings and the absorbent material.

The gel dressing of the present invention combines the actions of rehydration and absorption. These combined actions break down the necrotic tissue and remove slough from the wound. Thus, the dressing of the present invention has a debriding and cleansing action. It debrides necrotic tissue and then aids the removal of the debris resulting from the debridement. Furthermore, it cleanses the site of application by absorbing secretions such as blood, serum and purulent matter.

The dressing of the invention may be used to debride and halt the build up of cellular debris so preventing slough formation. Alternatively, where slough has already developed, the dressing's rehydrating action gently and effectively removes it without damaging fragile granulation tissue that may be present. Additionally, the dressing of the present invention is easily irrigated from the wound without harming fragile tissue.

The present invention will be illustrated by the following Examples.

EXAMPLE 1

A gel dressing of the invention having the following composition was made:

|  | % by weight |
| --- | --- |
| Akucell SW 3009-X181 Cross-linked sodium carboxymethyl cellulose | 3.00 |
| Monopropylene Glycol | 20.00 |
| Deionised water | 77.00 |
|  | 100.00 |

Polymer Slurry Component 50 kg of monopropylene glycol are stirred using a mixer. 18 kg of dry Akucell SW 3009-X181 Akzo Salt and Basic Chemicals are slowly added to the monopropylene glycol maintaining constant slow stirring, ensuring no lump formation occurs.

Bulk Liquid Component 70 kg of monopropylene glycol are transferred to a mixing vessel. 464.3 liters of purified water are then metered into the same vessel. The contents of the mixing vessel are mixed for upto 5 minutes eg. 2 minutes.

Mixing of Polymer Slurry Component and Bulk Liquid Component

If the slurry has been allowed to settle out, it must be re-stirred to ensure that the polymer is homogeneously dispersed. The slurry is then added to the bulk liquid component and thoroughly mixed. After the gel has formed and no further mixing is evident, the mixer is switched off.

The gel may be subsequently filled into suitable packaging, eg. 25 g sachets and sterilised.

EXAMPLE 2

A gel dressing of the invention having the following composition was made according to the precedure given in Example 1:

|  | % by weight |
| --- | --- |
| Akucell SW 3009-X181 Cross-linked sodium carboxymethyl cellulose | 10 |
| Monopropylene Glycol | 50 |
| Deionised Water | 40 |

EXAMPLE 3

A gel dressing of the invention having the following composition was made according to the precedure given in Example 1:

|  | % by weight |
| --- | --- |
| Akucell SW 3009-X181 Cross-linked sodium carboxymethyl cellulose | 10 |
| Monopropylene Glycol | 50 |
| Deionised Water | 40 |

The elasticity of the gels of the above was measured according to the above described procedure using the Cari-Med 100.

The results obtained are as follows:

|  | Elasticity Newtons/$M^2$ |
| --- | --- |
| Example 1 | 1500–2000 |
| Example 2 | 12870 |
| Example 3 | 10870 |

The results indicate that of the illustrated examples the gel of Example 1 is most suited for embodiments of the invention wherein the gel component is the sole component of the dressing.

EXAMPLE 4

This example is presented to illustrate the rehydration properties of the dressings of the present invention in comparison with the absorption properties of a prior dressing produced according to EP-A-0207022.

The product of Example 1 (A) was compared with a commericially available paste containing 64% dextranomer, DEG 600 and water (B).

Thus 25, 30 and 40% by weight gelatines were prepared and weighed (about 23 grams) after which a known weight of (A) or (B) were removed from the gelatine and the gelatine reweighed. The damage in weight of the gelatine in reported below.

|  | A | B |
| --- | --- | --- |
| 25 | +1.56 | −11.27 |
| 30 | +2.47 | −10.91 |
| 40 | +4.36 | −7.25 |

From the above result it is clearly shown that the prior art compositions are highly absorbent material whilst those of the present invention are not.

In a further aspect of the present invention, the gel may be filled into one compartment of a two compartment package. The other compartment may be used to hold a suitable backing layer such as an occlusive backing film or a layer of absorbent material which serves as a secondary dressing for use with the dressing of the present invention as hereinabove described.

I claim:

1. A wound dressing containing a water insoluble, water swellable cross-linked cellulose derivative selected from hydroxy lower alkylcelluloses having 1 to 6 carbon atoms and from carboxycelluloses, water and a polyol component, wherein the dressing comprises a gel which consists essentially of the cellulose derivative, water and polyol component and optionally one or more of wound therapeutic substances, active substances used as wound treatment agents; and the cellulose derivative comprises less than 10% by weight of the gel and wherein the gel promotes wound healing.

2. A dressing as claimed in claim 1 wherein the lower alkycellulose derivative is hydroxyethylcellulose or hydroxypropylcellulose.

3. A dressing as claimed in claim 1 wherein the carboxycellulose derivative is carboxymethylcellulose.

4. A dressing as claimed in claim 1 wherein the polyol component is a dihydroxyalkane having from 2 to 6 atoms.

5. A dressing as claimed in claim 4 wherein the dihydroxyalkane is 1,2-dihydroxypropane.

6. A dressing as claimed in claim 1 wherein the polyol component is a polyhydroxylalkane of the general formula:

$$C_nH_{(2n+2)}O_n$$

where n is a number from 3 to 6.

7. A dressing as claimed in any of claim 1 wherein the polyol component comprises polyethylene glycol.

8. A dressing as claimed in claim 7 wherein the polyethylene glycol has a molecular weight in the range of from 200 to 600.

9. A dressing as claimed in any of claim 1 wherein the polyol component is a diethylene or triethylene glycol.

10. A dressing as claimed in claim 1 wherein the polyol component comprises less than 50% by weight of the gel.

11. A dressing as claimed in claim 1 wherein the cellulose derivative comprises at least 0.1% by weight of the gel.

12. A dressing as claimed in claim 1 wherein the gel has been steam sterilised.

13. A dressing as claimed in claim 1 wherein the elasticity of the gel is greater than 300 Newtons/$M^2$ when measured using a Carri-med 100 CLF rheometer at 25° C., an oscillation reading of 5 Hz and a plates separation of 4.0 cm.

14. A dressing as claimed in claim 1 wherein the elasticity of the gel is less than 3000 Newtons/$m^2$ when measured using a Carri-med 100 CLF rheometer at 25° C., an oscillation reading of 5 Hz and a plate separation of 4.0 cm.

15. A dressing as claimed in claim 1 wherein the gel is a layer upon a backing layer.

16. A dressing as claimed in claim 15 wherein the backing layer is an occlusive film.

17. A dressing as claimed in claim 15 wherein the backing layer comprises a layer of an absorbent material.

18. A process for making the gel in the wound dressing as claimed in claim 1 comprising blending the cellulose derivative with at least some of the polyol component and thereafter adding the remaining components to the blend.

* * * * *